United States Patent [19]
Randell

[11] Patent Number: 5,868,670
[45] Date of Patent: Feb. 9, 1999

[54] ARTICLE OF MANUFACTURE FOR A BIOMEDICAL ELECTRODE AND INDICATOR

[75] Inventor: Werner A Randell, Milton, Wis.

[73] Assignee: Werner A. Randell, Sr., Milton, Wis.

[21] Appl. No.: 963,213

[22] Filed: Nov. 3, 1997

[51] Int. Cl.$^6$ ....................................................... A61B 5/00
[52] U.S. Cl. ............................................................ 600/372
[58] Field of Search ................................... 600/372, 382, 600/391, 396, 395, 397; 607/149, 152

[56] References Cited

U.S. PATENT DOCUMENTS

| | | |
|---|---|---|
| 4,657,023 | 4/1987 | Kuhn . |
| 4,674,512 | 6/1987 | Rolf . |
| 5,003,978 | 4/1991 | Dunseath, Jr. ........................... 600/391 |
| 5,330,527 | 7/1994 | Montecalvo et al. .................... 607/152 |
| 5,337,748 | 8/1994 | McAdams et al. ...................... 600/396 |

Primary Examiner—George Manuel

[57] ABSTRACT

An article of manufacture for a biomedical electrode and indicator with a nonconductive polymer backing material; the backing material to adhere, coat or attach the indicator and conductors, a pair of thin flexible conductors such as tin, silver or other such conductive medium. The conductors are made of dissimilar materials; an adhesive electrolyte substrate composing karaya, ionic polymer, electrode gel, or other like medium, said electrolyte is positioned between each conductor and conforms to the skin. The backing material provides an area of isolation between the paired conductors, and electrolyte. A thin flexible indicator affixed to the top of the backing material, said indicator having an conductive pattern for contact to each conductor. A path is created by the conductors, electrolyte and the body. The path is completed when the body comes in contact to the electrolyte, a potential created by two dissimilar conductors and an electrolyte provides the potential to the indicator. This disclosure also contemplates novel orientation of the conductors and electrolyte.

6 Claims, 1 Drawing Sheet

ARTICLE OF MANUFACTURE FOR A BIOMEDICAL ELECTRODE AND INDICATOR

BACKGROUND OF THE INVENTION

This invention relates generally to the field of disposable medical electrode for monitoring and diagnostic use, and more particularly to an article of manufacture for a biomedical electrode and indicator.

The elements of a electrode are known to the art. Electrodes generally comprise a conductive element, an ionic material and a terminal for connection to a lead wire. The prior art has made attempts to produce a biomedical electrode with low signal to noise ratio, and low impedance. Even with the use of prior art electrodes, the application of the electrode may be poor or improper. The quality of diagnostic medical recordings are inherently limited to the application of the electrode to the patient and the transmission of data to the recording device. Artifact and erroneous recordings stem from poor or improper application. This is detrimental to the diagnostic quality of the recordings.

To overcome the problems of improper application of the electrode a separate instrument known to the art is used to measure the impedance of the electrode. If an impedance meter were unavailable, the applicant would need to replace electrodes based upon the erroneous recording.

One of the major objectives of the present invention is to provide an indicator incorporated in the electrode. The applicant can get a visual indication of the quality when the electrode is placed on the subject. Without the need to use a separate instrument to check the quality of application, the cost and time needed for re-applying the electrode is reduced. The indicator quickly indicates poor or improperly attached electrodes; thus eliminating the artifact and erroneous recordings.

SUMMARY OF THE INVENTION

The primary object of the present invention is to provide an improved biomedical electrode that incorporates an indicator capable of displaying the quality of application to the body, which eliminates artifact and erratic EKG recordings characteristic of poor electrode application. Without the need for additional instruments to determine the quality of contact with a patient's skin, it reduces the time and cost of application by eliminating the need to re-apply the electrode. It can be easily applied, is self adhering, and readily conforms to the skin.

According to the present invention, there is a biomedical electrode and indicator comprising of a nonconductive flexible backing material, a pair of thin flexible conductors, an adhesive electrolyte substrate, and a flexible indicator affixed to the top of the backing material.

The backing material is to provide a surface to adhere, coat or attach the indicator and conductors to, and provides a means for a conductive pattern to each of the conducts and the indicator. The backing material provides isolation thermally, and electrically from the patient.

The conductors are metal foil layers such as tin, silver, or other such conductive medium, which may adhere to or coated to the backing material.

The electrolyte is composed of karaya, ionic polymer, electrode gel, or other like medium, said electrolyte is applied to each conductor and conforms to the skin. The conductors and electrolyte are substantially of like surface area. The electrolyte is spaced on the conductors so that no contamination takes place from one element to another element of the electrode during any stage of handling.

A major goal is accomplished through the use of conductors that are made of dissimilar materials. This goal is to produce a D.C. offset, and apply that current to the indicator. The term "D.C. offset" refers to a minute current produced by the eletro-chemical makeup of the electrode itself. The novel use of this D.C. offset is a major goal of the present invention. The greater the D.C. offset applied to the indicator, the greater the value displayed.

In prior art, generally this D.C. offset is detrimental to the ECG recording. By the novel orientation of the conductors and the use of the backing material as an insulator, the present invention overcomes this problem. The conductors are spaced apart on the backing material. This spacing provides the area of electrical isolation between the paired conductors and electrolyte. Using only one of the conductor's as a terminal to the medical recording device, the path for the generated D.C. offset is to the indicator; not the medical device. Moreover, the conductor providing the the terminal to the recorder will have a very low noise to signal ratio.

The indicator is a thermochromic device, and produces a visual display of the current generated by the D.C. offset. Another object of the present invention is the use of electrolyte and the subject's body as a path. The circuit is completed when the body comes in contact to the electrolyte. The current generated by two dissimilar conductors and an electrolyte are then applied to the indicator.

Other objects and advantages of the present invention will become apparent from the following descriptions taken in connection with the accompanying drawings; wherein, by way of illustration and example, an embodiment of the present invention is disclosed.

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood; however, that the present invention may be embodied in various forms. Therefore, specific details disclosed herein are not to be interpreted as limiting, but rather as a basis for the claims and as a representative basis for teaching one skilled in the art, to employ the present invention in virtually any appropriately detailed system, structure or manner. Moreover, it should be understood that the present invention can be used in many types of electrode form including those with snaps.

Figure 1:
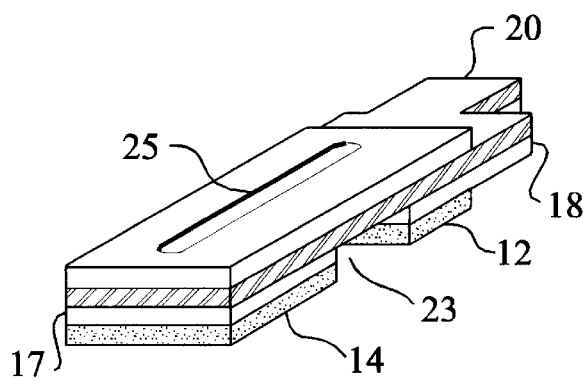
FIG. 1 is a perspective view of the invention.
Figure 4:
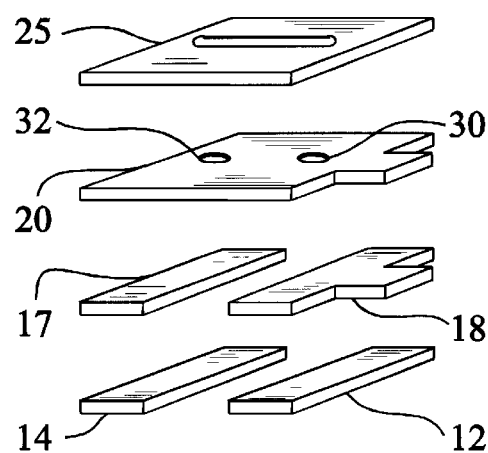
FIG. 4 is an exploded view of the invention.

Upon inspection of FIG. 1, it will be seen that biomedical electrode shown has items typical in a medical electrode. One skilled in the art will appreciate the basic function of these items, as shown in FIG. 1, items 12,14 are the electrolyte. It is found in practice that the electrolyte provides adhesion to the skin and an electrical path between the subject's skin and conductor, shown as items 18,17 in FIG. 1. Moreover, it is shown that FIG. 1, item 18 is a conductor providing an electrical path between the electrolyte and the lead wire. In like manner, FIG. 1, item 11 is a backing material used to provide a surface to adhere, coat or attach the conductors and indicator.

Figure 2:
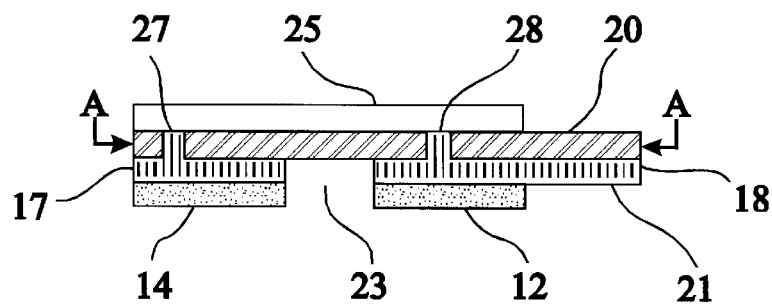
FIG. 2 is a cross sectional view of the invention.

Upon inspection of FIG. 2, it should be noted that a thin flexible indicator, item 25 is affixed to the backing material item 11. One of the features of the invention is two separate conductors, items 17,18. The items 12,14, are the electrolyte areas. FIG. 2 shows areas of contact, items 27,28 with the indicator, item 25, through the backing material, item 11 providing a conductive area for the indicator. The electrical connection of the indicator to the conductors may be done in various ways without departing from my invention. Moreover a space is shown, item 23 providing separation of the conductors, items 17,18 and electrolyte areas, items 12,14. The electrolyte is spaced on the conductors so that no contamination takes place from one element to another element of the electrode during any stage of handling.

Figure 3:
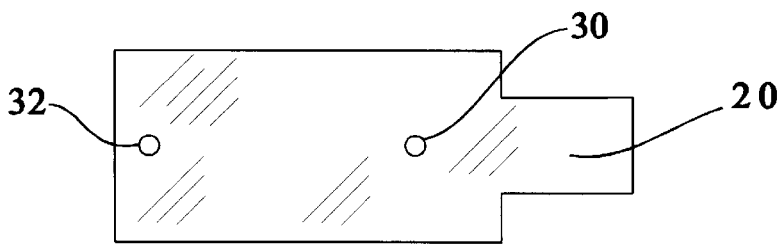
FIG. 3 is a cross sectional view of the invention along the line A—A.

The function of the backing material, FIG. 2 item 11, may be understood upon reference to FIG. 3. The backing material, FIG. 3, item 11 is nonconductive for the purpose of providing electrical isolation of the conductors. This electrical isolation is accomplished by spacing the conductors on the backing material. The backing material has areas, FIG. 3, items 30,32 to provide an area of contact with the indicator and the conductors.

The pair of thin flexible conductors of FIG. 2 items 17,18 differ primarily in that each conductor is composed of a different or dissimilar metals or conductive material. The conductive medium may be; but not limited to, tin, silver, conductive ink or other such material. Nevertheless, an area of each conductor is made to provide an electrical path to the indicator. Moreover, the exposed area of one of the conductors, FIG. 2, item 21, provides an electrical path for the lead wire. An important goal of the present invention should be noted; the path of conduction to the lead is electrically isolated from the D.C. offset created by the two conductors and electrolyte. For the purpose of providing electrical isolation, the conductors are spaced apart, FIG. 2, item 23 from one another on the backing material.

Having observed the details of the conductors, attention may now be given to the electrolyte. The electrolyte, FIG. 2, items 12,14 are composed of karaya, ionic polymer, electrode gel or other like medium and acts as an adhesive to the subject's skin. The electrolyte, FIG. 2, item 12,14 is positioned on each conductor, FIG. 2, items 17,18 and conforms to the the skin when the electrode is applied. The spacing, FIG. 2, item 23 of the electrolyte maintains the electrical isolation of the conductors. This electrical isolation is maintained until the electrode is applied to the skin.

Pursuant to the invention, a thermochormatic indicator, FIG. 2 item 25 is affixed to the top of the backing material. Two areas of electrical contact are provided with the conductors through the backing material. The indicator changes value in relation to a potential created by the conductors and electrolyte. The potential is directly proportional to the quality of contact with the patient's skin, so that a visual gauge is displayed on the indicator, dependant and relative to the potential developed.

An important goal of the present invention to be noted is a path created by the conductors, electrolyte, indicator and the subject's body. When the electrode is applied to the skin, a D.C. offset is created by the two dissimilar conductors and electrolyte so that it acts as a battery. This potential is applied to the indicator by paths provided through the backing material, FIG. 3 items 30,32.

While the invention has been described in connection with a preferred embodiment, it is not intended to limit the scope of the invention to the particular form set forth; but on the contrary, it is intended to cover such alternatives, modifications, and equivalents as may be included within the spirit and scope of the invention as defined by the appended claims.

What is claimed is:

1. An article of manufacture for a biomedical electrode and indicator comprising, a nonconductive polymer backing material, said backing material to adhere, coat or attach the indicator and a pair of thin flexible conductors such as tin, silver or other such conductive medium; said conductors are made of dissimilar materials; an adhesive electrolyte substrate composing karaya, ionic polymer, electrode gel, or other like medium; said electrolyte is positioned between each conductor and conforms to the skin; the conductors and electrolyte are substantially of like surface area; an area of the backing material provides an area of isolation between the paired conductors and electrolyte; a thin, flexible indicator affixed to the top of the backing material; said indicator having an electrical connection for each conductor; a circuit created by the conductors, electrolyte and the body; the circuit is completed when the body comes in contact to the electrolyte; a potential created by two dissimilar conductors and an electrolyte providing a transmission of the potential to the indicator.

2. An article of manufacture for a biomedical electrode and indicator as claimed in claim 1 further comprising: a means for said indicator to provide visual display proportional to a potential created to thereby achieve optimum application of the electrode.

3. An article of manufacture for a biomedical electrode and indicator as claimed in claim 1 further comprising a circuit created by the conductors, electrolyte and the body so that it acts as a battery creating a D.C. offset potential; said potential is dependant on the quality of contact to the patient's skin.

4. An article of manufacture for a biomedical electrode and indicator as claimed in claim 1 further comprising a novel structure for connection of the conductors to said indicator.

5. An article of manufacture for a biomedical electrode and indicator as claimed in claim 1 wherein said backing material provides the electrical and thermal isolation between patient and indicator eliminating any transient contamination.

6. An article of manufacture for a biomedical electrode and indicator as claimed in claim 1 further comprising a novel means for effectively spacing the conductors and electrolyte so that no contamination takes place from one element to another element of the electrode during any stage of handling.

* * * * *